US00PP12797P2

(12) United States Plant Patent
Ruigrok-van Haaster

(10) Patent No.: US PP12,797 P2
(45) Date of Patent: Jul. 23, 2002

(54) DAHLIA PLANT NAMED 'RIO GRANDE'

(76) Inventor: Ans Ruigrok-van Haaster, Hyacintenlaan 15, 2182 DE Hillegom (NL)

( * ) Notice: Subject to any disclaimer, the term of this patent is extended or adjusted under 35 U.S.C. 154(b) by 0 days.

(21) Appl. No.: 09/838,941

(22) Filed: Apr. 23, 2001

(51) Int. Cl.[7] ..... A01H 5/00

(52) U.S. Cl. ..... Plt./321

(58) Field of Search ..... Plt./321

(56) References Cited

U.S. PATENT DOCUMENTS

PP10,124 P * 11/1997 Kleinhanns ..... Plt./321

* cited by examiner

*Primary Examiner*—Kent L. Bell
(74) *Attorney, Agent, or Firm*—C. A. Whealy

(57) ABSTRACT

A distinct cultivar of Dahlia plant named 'Rio Grande', characterized by its upright, uniformly mounded and compact plant habit; freely branching habit; short response time; continuously and freely flowering during the spring until fall; full inflorescences with multiple rows of ray florets; and dark pink-colored ray florets with bright yellow-colored disc florets.

1 Drawing Sheet

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the name 'Rio Grande'.

The new Dahlia is a product of a planned breeding program conducted by the Inventor in Hillegom, The Netherlands. The objective of the breeding program is to create new pot-type Dahlia cultivars with desirable inflorescence form, attractive colors, and good garden performance.

The new Dahlia originated from a cross made by the Inventor in 1995 of two unidentified proprietary *Dahlia variabilis* seedling selections, not patented. The new Dahlia was discovered and selected by the Inventor as a single flowering plant within the progeny of the stated cross grown in a controlled environment in Hillegom, The Netherlands. The selection of this plant was based on its desirable inflorescence form and attractive floret colors.

Asexual reproduction of the new Dahlia by vegetative tip cuttings was first conducted in Hillegom, The Netherlands in 1996. Asexual reproduction by cuttings has shown that the unique features of this new Dahlia are stable and reproduced true to type in successive generations.

SUMMARY OF THE INVENTION

The cultivar 'Rio Grande' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rio Grande'. These characteristics in combination distinguish 'Rio Grande' as a new and distinct pot-type Dahlia:

1. Upright, uniformly mounded and compact plant habit.
2. Freely branching, full and dense plants.
3. Short response time.

4. Continuously and freely flowering during the spring until fall.
5. Full inflorescences with multiple rows of ray florets.
6. Dark pink-colored ray florets with bright yellow-colored disc florets.

Plants of the new Dahlia differ from plants of the parent selections primarily in ray floret color.

Plants of the new Dahlia can be compared to plants of the cultivar 'Maryland', disclosed in U.S. Plant Pat. No. 11,602. However, in side-by-side comparisons conducted in De Lier, The Netherlands, plants of the new Dahlia differed from plants of the cultivar 'Maryland' in the following characteristics:

1. Plants of the new Dahlia grow faster and flower about one to two weeks earlier than plants of the cultivar 'Maryland'.
2. Plants of the new Dahlia have smaller leaves than plants of the cultivar 'Maryland'.
3. Plants of the new Dahlia have smaller inflorescences than plants of the cultivar 'Maryland'.
4. Plants of the new Dahlia and the cultivar 'Maryland' differ in ray floret color.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of a typical flowering plant of 'Rio Grande' that was grown in a 14-cm container for about 8 weeks.

DETAILED BOTANICAL DESCRIPTION

In the following description, color references are made to The Royal Horticultural Society Colour Chart except where general terms of ordinary dictionary significance are used. The following observations and measurements describe plants grown and flowered during the fall in a glass-covered greenhouse in De Lier, The Netherlands. One rooted cutting was planted in a 14-cm container and pinched one week after planting. During the production of these plants, the day temperature ranged from 19 to 24° C., night temperatures ranged from 18 to 21° C., and light levels ranged from 10,000 to 15,000 lux. Measurements and numerical values represent averages of typical flowering plants about 8 weeks after planting.

Botanical classification: *Dahlia variabilis* cultivar 'Rio Grande'.

Commercial classification: Pot-type Dahlia.

Parentage:

*Female, or seed, parent.*—Proprietary *Dahlia variabilis* seedling selection, not patented.

*Male, or pollen, parent.*—Proprietary *Dahlia variabilis* seedling selection, not patented.

Propagation:

*Type.*—Terminal tip cuttings.

*Time to initiate roots.*—Summer: About 5 days at 22° C. Winter: About 8 days at 20° C.

*Time to produce a rooted cutting.*—Summer: About 12 days at 22° C. Winter: About 16 days at 20° C.

*Root description.*—Fine and fibrous.

*Rooting habit.*—Freely branching; development of tubers has not been observed.

Plant description:

*Appearance.*—Herbaceous pot-type Dahlia. Inverted triangle; stems mostly upright and somewhat outwardly spreading giving a uniformly mounded appearance to the plant; relatively compact. Freely branching, lateral branches develop at every node after removal of terminal apex (pinching); dense and full plants. Moderately vigorous.

*Plant height.*—About 29.5 cm.

*Plant width or area of spread.*—About 25.5 cm.

*Lateral branches.*—Length: About 25 cm. Diameter: About 5 mm. Internode length: About 2 cm. Strength: Moderately strong, flexible. Texture: Smooth, glabrous. Color: 165A.

*Foliage description.*—Arrangement: Leaves compound with three or five leaflets; opposite. Terminal leaflet length: About 4 cm. Terminal leaflet width: About 3 cm. Shape: Ovate. Apex: Acute. Base: Attenuate. Margin: Serrate. Texture, both surfaces: Slightly pubescent. Venation pattern: Pinnate. Color: Young foliage upper surface: 137A. Young foliage lower surface: 138B. Mature foliage upper surface: 147A; venation, 146D. Mature foliage lower surface: 138B; venation, 137C. Petiole: Length: About 1.5 cm. Diameter: About 3 mm. Color: 165A.

Inflorescence description:

*Appearance.*—Terminal and axillary inflorescences held above the foliage on strong flexible peduncles. Composite inflorescence form with elongated oblong-shaped ray florets and disc florets massed at the center; ray and disc florets arranged acropetally on a capitulum. Inflorescences not fragrant. Inflorescences persistent.

*Flowering response.*—Plants flower continuously and freely from the spring through the fall.

*Response time* (*time to flowering*).—Plants begin flowering about 6 to 7 weeks after planting rooted cuttings.

*Postproduction longevity.*—Inflorescences maintain good color and substance for about two weeks on the plant.

*Quantity of inflorescences.*—*More than* 20 open inflorescences and buds per plant.

*Inflorescence bud* (*before showing color*).—Shape: Globular, roughly spherical. Length: About 5 mm. Diameter: About 5 mm. Color: 144B.

*Inflorescence size.*—Diameter: About 3.25 cm. Depth (height): About 1.25 cm. Disc diameter: About 5 mm. Receptacle diameter: About 1.75 cm. Receptacle height: About 5 mm.

*Ray florets.*—Shape: Elongated-oblong. Orientation: Initially upright, outer florets perpendicular to peduncle. Aspect: Straight, concave. Length: About 1.5 cm. Width: About 5 mm. Apex: Rounded to acute. Base: Cuneate; short corolla tube. Margin: Entire. Texture, both surfaces: Smooth, glabrous. Number of ray florets per inflorescence: About 50 in about 6 or 7 rows. Color: When opening and fully opened, upper surface: Towards apex, 67B; towards base, 57A; becoming darker towards base to 60A with subsequent development. When opening and fully opened, lower surface: 75B.

*Disc florets.*—Shape: Tubular, elongated. Apex: Rounded. Length: About 1 cm. Width: Apex: About 2.5 mm. Base: About 1 mm. Number of disc florets per inflorescence: About 45 to 50. Color: Immature: 15B. Mature: Apex: 14A. Mid-section: 8B. Base: 145C.

*Involucral bracts.*—Quantity: About 7 or 8 per inflorescence. Length: About 1.25 cm. Width: About 6 mm. Shape: Ovate to spatulate. Apex: Acute. Base: Cuneate. Margin: Entire. Texture, both surfaces: Smooth. Color: Upper surface: 137B. Lower surface: 143C.

*Peduncles.*—Length, terminal inflorescence: About 5 cm. Diameter: About 2 mm. Aspect: Erect. Strength: Moderately strong, flexible. Texture: Smooth, glabrous. Color: 165A.

*Reproductive organs.*—Androecium: Present on disc florets only. Stamen quantity: Four per floret. Anther length: About 2 mm. Anther shape: Ovoid. Anther color: 14A. Pollen amount: Moderate. Pollen color: 23A. Gynoecium: Present on both ray and disc florets. Pistil quantity: One per floret. Pistil length: About 9 mm. Stigma color: 14A. Style length: About 8 mm. Style color: 7B. Ovary color: 1C.

*Seed production.*—Seed production has not been observed.

Disease/pest resistance: Resistance to pathogens or pests common to Dahlias has not been observed on plants grown under commercial greenhouse or outdoor conditions.

Weather tolerance: Plants of the new Dahlia have been observed to be wind and rain-tolerant. Plants of the new Dahlia tolerant temperatures from 1° to 40° C.

It is claimed:

1. A new and distinct cultivar of Dahlia plant named 'Rio Grande', as illustrated and described.

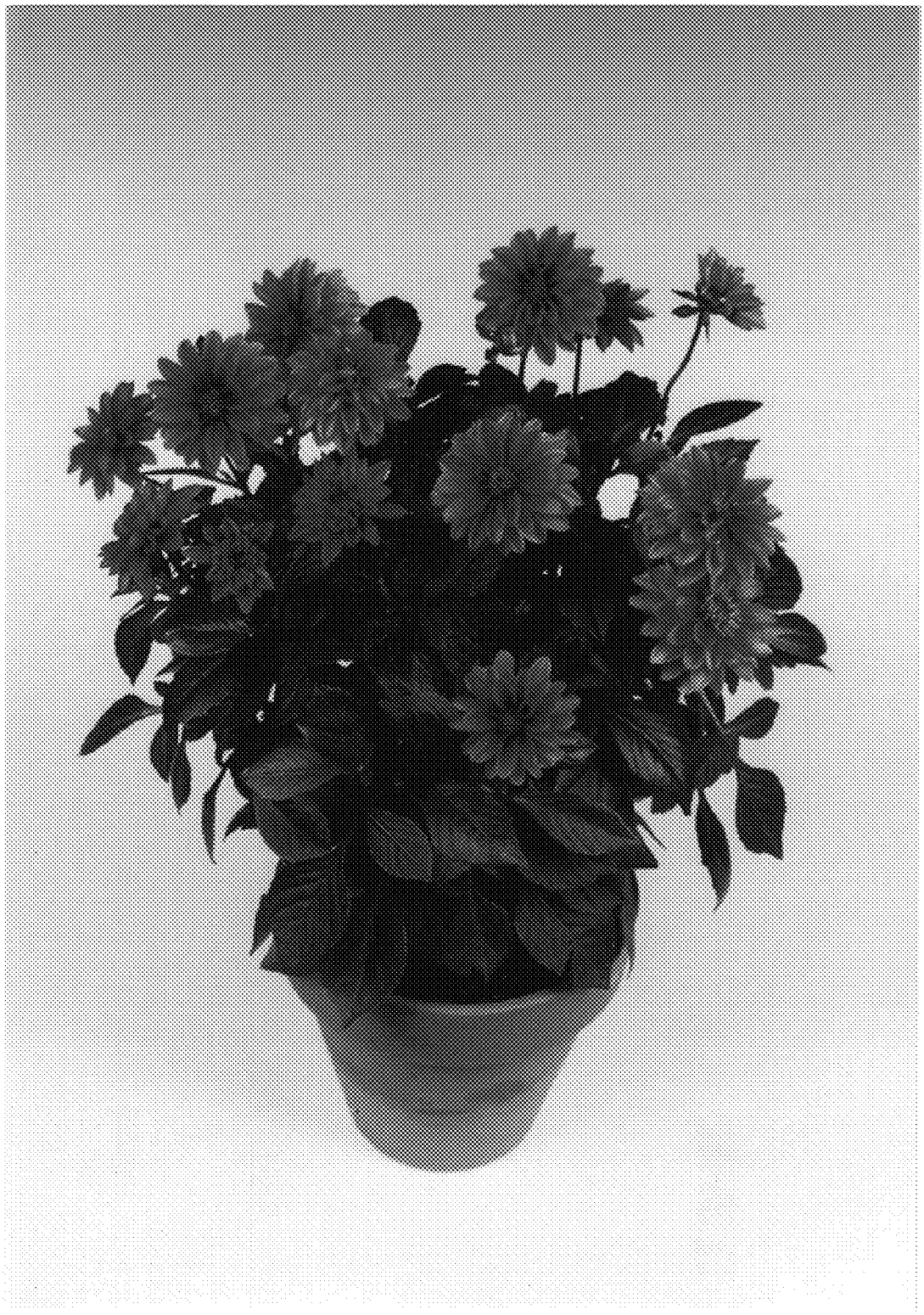

* * * * *